United States Patent

Hegel

(10) Patent No.: US 10,435,187 B2
(45) Date of Patent: Oct. 8, 2019

(54) RECAPPER, LABORATORY AUTOMATION SYSTEM, AND METHOD OF RECAPPING A SAMPLE CONTAINER

(71) Applicant: Roche Diagnostics Operations, Inc., Indianapolis, IN (US)

(72) Inventor: Markus Hegel, Waiblingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 198 days.

(21) Appl. No.: 15/729,066

(22) Filed: Oct. 10, 2017

(65) Prior Publication Data

US 2018/0029731 A1 Feb. 1, 2018

Related U.S. Application Data

(63) Continuation of application No. PCT/EP2016/059353, filed on Apr. 24, 2016.

(30) Foreign Application Priority Data

Apr. 27, 2015 (EP) .................................. 15165249

(51) Int. Cl.
*B65B 7/28* (2006.01)
*G01N 35/04* (2006.01)
*G01N 1/00* (2006.01)
*G01N 35/10* (2006.01)

(52) U.S. Cl.
CPC .......... *B65B 7/2878* (2013.01); *B65B 7/2807* (2013.01); *G01N 35/04* (2013.01); *G01N 2001/002* (2013.01); *G01N 2035/0403* (2013.01); *G01N 2035/0405* (2013.01); *G01N 2035/1093* (2013.01)

(58) Field of Classification Search
CPC ... B65B 7/2878; B65B 7/2807; B65B 7/2814; G01N 2035/0405; G01N 2035/0403; B01L 2300/04; B01L 2300/041; B01L 2300/042; B01L 2300/004
See application file for complete search history.

(56) References Cited

U.S. PATENT DOCUMENTS

| | | | | |
|---|---|---|---|---|
| 3,523,355 A | * | 8/1970 | Schlapkohl | B65B 7/28 29/240 |
| 3,628,307 A | * | 12/1971 | Croasdale | B65B 7/2807 53/299 |
| 3,755,987 A | | 9/1973 | Dardaine et al. | |
| 3,864,898 A | * | 2/1975 | West | B65B 7/2807 53/328 |
| 3,905,178 A | * | 9/1975 | West | B65B 7/2807 53/328 |
| 3,908,340 A | * | 9/1975 | Erhardt | B29C 65/18 53/307 |
| 4,065,909 A | * | 1/1978 | Mueller | B65B 7/168 53/420 |

(Continued)

FOREIGN PATENT DOCUMENTS

| | | |
|---|---|---|
| FR | 2653408 A1 | 4/1991 |
| WO | 2003034038 A2 | 4/2003 |
| WO | 2010/131457 A1 | 11/2010 |

*Primary Examiner* — Brian R Gordon
(74) *Attorney, Agent, or Firm* — Roche Diagnostics Operations, Inc.

(57) ABSTRACT

A recapper for placing foils on laboratory sample containers is presented. The foils are brought on the sample container by a lever arrangement that is rotated around a vertical axis.

17 Claims, 1 Drawing Sheet

(56) References Cited

U.S. PATENT DOCUMENTS

| | | | | |
|---|---|---|---|---|
| 4,075,820 | A * | 2/1978 | Standley | B29C 65/0672 53/329.4 |
| 4,494,363 | A * | 1/1985 | Rica | B65B 55/022 53/109 |
| 4,575,987 | A * | 3/1986 | Fortuna | B65B 7/2878 53/298 |
| 4,601,160 | A * | 7/1986 | Heisler | B65B 7/2842 193/47 |
| 4,779,748 | A * | 10/1988 | King | B65B 7/2807 215/256 |
| 4,816,110 | A | 3/1989 | Foldesi et al. | |
| 5,032,213 | A * | 7/1991 | Thomas, Jr. | B29C 65/18 156/498 |
| 5,599,505 | A * | 2/1997 | Fujisaki | B01L 9/52 206/499 |
| 5,617,973 | A * | 4/1997 | Seto | G01N 35/00029 221/279 |
| 5,673,814 | A * | 10/1997 | Terashima | F16F 1/128 221/227 |
| 6,418,701 | B1 * | 7/2002 | Navarro | B65B 7/2807 221/223 |
| 2003/0182901 | A1 * | 10/2003 | Savage | B65B 3/045 53/468 |
| 2006/0054572 | A1 * | 3/2006 | Sygall | B01L 3/505 210/787 |
| 2006/0242927 | A1 * | 11/2006 | Gorzynski | B65B 7/2807 53/287 |
| 2008/0233015 | A1 * | 9/2008 | Turner | B01L 3/50851 422/400 |
| 2011/0120998 | A1 * | 5/2011 | Brauer | B65B 7/01 220/265 |
| 2011/0293488 | A1 * | 12/2011 | Nichols | B01L 3/50853 422/500 |
| 2011/0306053 | A1 * | 12/2011 | Ochsenbein | B01L 7/52 435/6.12 |
| 2014/0260118 | A1 * | 9/2014 | Knight | B01L 3/50825 53/492 |
| 2014/0315325 | A1 * | 10/2014 | Cobb | B01L 3/5023 436/174 |
| 2016/0325284 | A1 * | 11/2016 | Camillo | B01L 3/5025 |
| 2017/0269112 | A1 * | 9/2017 | Gerstel | B04B 5/0414 |
| 2017/0305586 | A1 * | 10/2017 | Rizzi | B29C 65/7888 |
| 2019/0016487 | A1 * | 1/2019 | Capitani | B29C 65/7888 |
| 2019/0185188 | A1 * | 6/2019 | Palumbo | B65B 11/52 |

\* cited by examiner

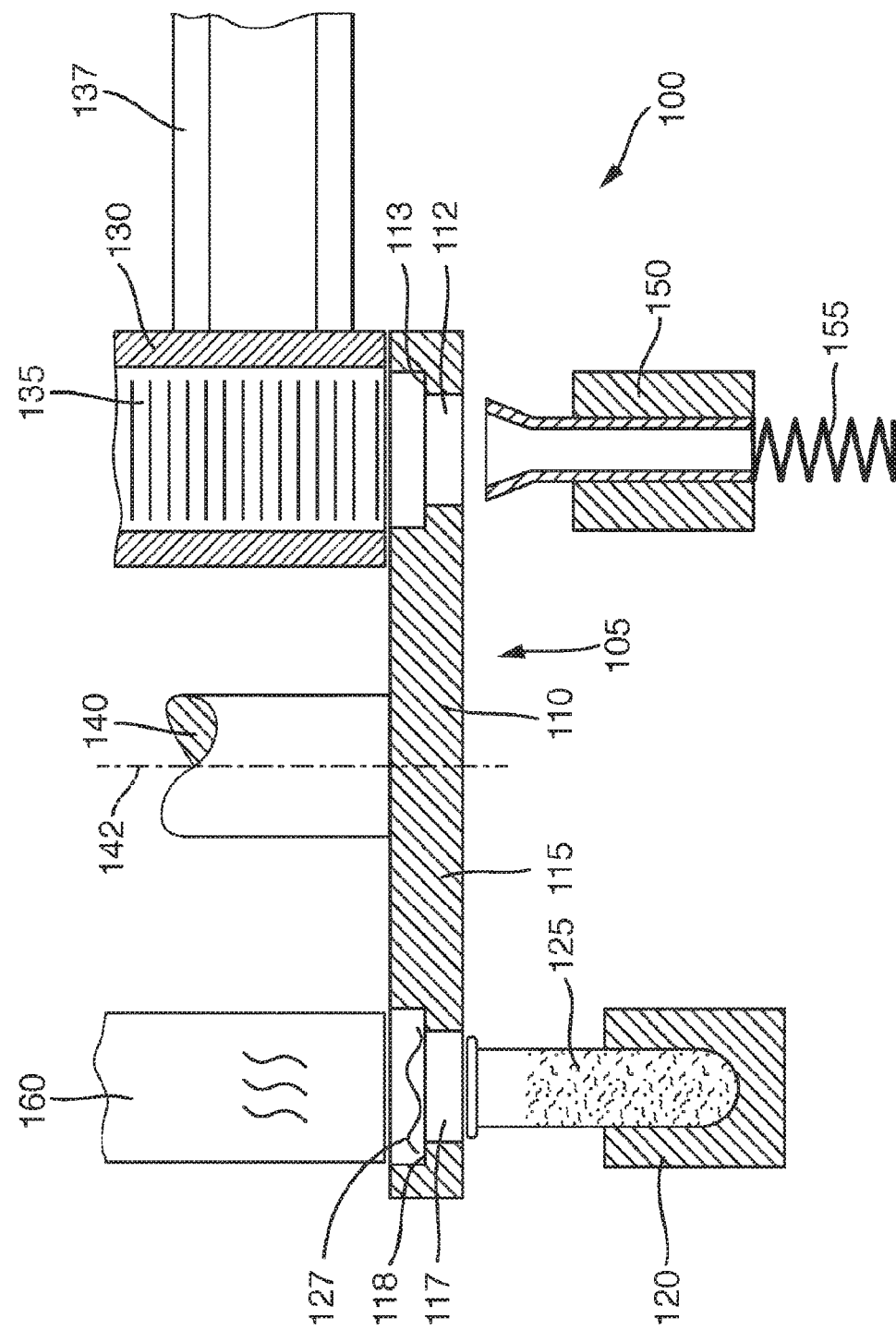

RECAPPER, LABORATORY AUTOMATION SYSTEM, AND METHOD OF RECAPPING A SAMPLE CONTAINER

CROSS-REFERENCE TO RELATED APPLICATIONS

This application is a continuation of PCT/EP2016/059353, filed Apr. 27, 2016, which is based on and claims priority to EP 15165249.2, filed Apr. 27, 2015, which are hereby incorporated by reference.

BACKGROUND

The present disclosure generally relates to a recapper for placing foils on laboratory sample containers, to a laboratory automation system comprising such a recapper, and to a method of recapping a sample container.

Laboratory automation systems typically comprise a number of pre-analytical, analytical and/or post-analytical stations that are used to handle samples contained in sample containers. Such sample containers can, for example, be embodied as laboratory tubes. After a sample has been processed in a station, it is often desirable to place a foil or a cap on the sample container in order to prevent spilling of the sample out of the sample container and in order to prevent contamination.

For that purpose, recappers can be used that automatically place/replace and secure foils on sample containers. However, such recappers can be a bottleneck in a laboratory automation system, thus limiting throughput.

Therefore, there is a need for a recapper that is adapted to operate with a high throughput, a laboratory automation system comprising such a recapper, and a method of recapping a sample container that is adapted for a high throughput.

SUMMARY

According to the present disclosure, a recapper for placing foils on laboratory sample containers is presented. The recapper can comprise a foil magazine and a sample container holder horizontally distant from the foil magazine. The sample container holder can be adapted to hold a sample container. The recapper can also comprise a lever arrangement comprising a plurality of levers. Each lever can comprise a foil transport element. Each foil transport element can be a through-hole extending vertically through a corresponding lever with a landing for holding the foil inside the through-hole. The recapper can also comprise a rotating device. Each lever can be attached to the rotating device such that with rotation of the rotating device, each lever rotates horizontally between a first orientation and a second orientation. In the first orientation, the foil transport element of the lever can be positioned at the foil magazine for collecting a foil from the foil magazine. In the second orientation, the foil transport element of each lever can be positioned at the sample container holder to place the foil on the sample container.

Accordingly, it is a feature of the embodiments of the present disclosure to provide for a recapper that is adapted to operate with a high throughput, to provide for a laboratory automation system comprising such a recapper, and to provide for a method of recapping a sample container that is adapted for a high throughput. Other features of the embodiments of the present disclosure will be apparent in light of the description of the disclosure embodied herein.

BRIEF DESCRIPTION OF THE DRAWING

The following detailed description of specific embodiments of the present disclosure can be best understood when read in conjunction with the following drawing, where like structure is indicated with like reference numerals and in which:

FIG. 1 illustrates a recapper according to an embodiment of the present disclosure.

DETAILED DESCRIPTION

In the following detailed description of the embodiments, reference is made to the accompanying drawing that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A recapper for placing/replacing foils and/or caps on laboratory sample containers is presented. The recapper can comprise a foil magazine. The recapper can further comprise a sample container holder horizontally distant from the foil magazine. The sample container holder can be adapted to hold a sample container. The sample container holder can be adapted to hold the sample container in an upright orientation and/or in a recapping position. The recapper can further comprise a lever arrangement comprising a plurality (e.g., an integer multiple of 2) of levers. Each lever can have or comprise a respective foil transport element. The recapper can further comprise a rotating device.

Each lever can be attached to the rotating device such that with rotation of the rotating device, the lever rotates in a substantially horizontally aligned plane. Especially, the lever can rotate about a substantially vertical axis. The lever can rotate between a first orientation and a second orientation. It may be noted that also further orientations (third, fourth, etc., orientations) can be possible.

In the first orientation, the foil transport element of the lever can be positioned at, or located at, (e.g. positioned below) the foil magazine for collecting a foil from the foil magazine. In the second orientation, the foil transport element of the lever can be positioned at, or located at, (e.g. positioned above) the sample container holder to place the foil on the sample container.

With the recapper, it can be possible to significantly increase throughput compared to recappers known from the prior art. Especially, rotating levers can be operated significantly faster than linear transport mechanisms that are typically used in prior art recappers.

The recapper may take out foils from the foil magazine and transport them to the sample container at high speed. Afterwards, the foil can be secured to the sample container. The same can be done with caps if they are contained in the foil magazine. Thus, the recapper can, in general, be used both with foils and with caps. It can be noted that whenever the word "foil" is used in the specification, the word "cap" can also be used. This disclosure can thus comprise usage of foils and caps equally.

According to an embodiment, the foil magazine can be positioned above the lever arrangement. The foils, or caps, contained in the foil magazine can thus easily be taken out in order to be positioned in the foil transport element by pulling it out of the magazine in a downward direction. Alternatively, the magazine can, for example, be adapted to let a foil fall out of the magazine.

According to an embodiment, a vacuum device can be positioned below the lever arrangement, and in one embodiment, directly below the foil magazine, for moving the foil from the foil magazine in a foil transport element placed below. Such a vacuum device may be adapted to move through the foil transport element to the foil magazine to abut the foil and to apply a vacuum to the foil for securing the foil to the vacuum device. The vacuum device may further be adapted to be lowered from the foil magazine in a position in which the foil is contained in the foil transport element and to release the foil by ceasing application of the vacuum. With such a vacuum device, foils can easily be removed from the foil magazine and can be placed in the foil transport element of the respective lever. The vacuum device may be driven by a link motion and/or by a spring. In one embodiment, vertical motion of the vacuum device can be driven in such a way. It may be noted that in a typical implementation, the vacuum device can penetrate through a hole in the lever that can be defined by the respective foil transport element.

According to an embodiment, the rotating device can be adapted to move the lever arrangement between an upper position and a lower position. In the upper position, the lever arrangement can rotate freely. In the lower position, the foil contained in a foil transport element can abut the sample container. With such an arrangement, a vertical distance between an upper side of a sample container on which the foil can be placed and a lower side of the foil magazine can be accounted for. Typically, a lever that has just loaded a foil below the foil magazine can be rotated while in the upper position such that the foil can be positioned above the sample container. The lever can be subsequently lowered such that the foil can abut the sample container and can be secured to the sample container, for example, by heating.

According to an embodiment, the sample container holder can be positioned below the lever arrangement such that the sample container held in the sample container holder can be positioned below the lever arrangement. The sample container holder can be positioned such that a foil transport element of a lever can be positioned above the sample container holder when the respective lever is in its second orientation.

According to an embodiment, a heating device can be positioned above the lever arrangement and can be operable to heat a foil after the foil has been brought into contact with the sample container by a lever. Such a heating device can be used in order to seal the sample container with the foil. It can, however, be noted that also other methods for securing a foil on a sample container can be used, for example, by using adhesives or by using positive connections.

According to an embodiment, the heating device can be adapted to move between an upper position and a lower position. In the lower position, the heating device can abut a foil in contact with a sample container held in the sample container holder. Such an implementation can be used in order to allow free rotation of a lever when the heating device is in its upper position and to allow sealing of a foil to a sample container by lowering the heating device. It can be noted that in a typical implementation, the heating device can comprise a number of resistive heaters in order to heat the foil.

Each foil transport element can be embodied as a through-hole extending substantially vertically through a corresponding lever with a landing, or step, for holding the foil inside the through-hole. By such an arrangement, a foil can be taken out of the foil magazine and can be placed on the landing, especially during transport to the sample container. Typically, an inside part of the through-hole at and below the landing can also be free of any material, such that, for example, a vacuum device, as discussed above, can penetrate through the through-hole and can abut a foil being held in the foil magazine.

According to an embodiment, all levers of the lever arrangement can be arranged with equal angle between the levels in a substantially horizontal plane. This can simplify construction and operation of the recapper.

According to an embodiment, the lever arrangement can comprise a first lever and a second lever. The first lever and the second lever can be arranged with an angle of about 180° between them in a substantially horizontal plane. Such an arrangement with two levers has been proven suitable for a fast and reliable operation of the recapper. In such a case, the rotating device may especially be adapted to rotate the lever arrangement by an angle of about 180°.

According to an embodiment, the rotating device can solely be adapted to rotate the lever arrangement by a specific angle, preferably about 180°, in both rotating directions. Usage of both rotating directions can significantly simplify construction of the rotating device, especially compared with implementations that can require continuous rotational motion in one rotational direction.

According to an embodiment, the recapper can comprise a foil magazine handling device adapted to change and/or move the foil magazine. This can be used in order to automatically change the foil magazine. For example, in the case when a foil magazine is empty, a newly supplied foil magazine fully loaded can be transported to the place where the empty foil magazine was placed before. The empty foil magazine can be removed. This can allow an even higher degree of automation, thus minimizing need for manual operation.

According to an embodiment, the recapper can comprise a sample container exchange device adapted to exchange or replace a sample container held in the sample container holder after recapping by another sample container. This can allow for automatic exchange of sample containers after a specific sample container has been sealed with a foil. Especially in this case, automatic operation can significantly increase throughput compared with manual operation.

A laboratory automation system is presented. The laboratory automation system can comprise a number of pre-analytical, analytical and/or post-analytical stations. It can further comprise a recapper as described above. The recapper can be adapted to weld foils on sample containers containing samples that are to be processed or have been processed by one or more of the stations.

Pre-analytical stations may be adapted to perform any kind of pre-processing of samples, sample containers and/or sample container carriers.

Analytical stations may be adapted to use a sample or part of the sample and a reagent to generate a measuring signal. The measuring signal can indicate if and in which concentration, if any, an analyte exists.

Post-analytical stations may be adapted to perform any kind of post-processing of samples, sample containers and/or sample container carriers.

It can be noted that all embodiments, implementations or other details as discussed herein with respect to the recapper can also be applied to the recapper of the laboratory automation system.

The pre-analytical, analytical and/or post-analytical stations may comprise at least one of a decapping station, a recapping station, an aliquot station, a centrifugation station, an archiving station, a pipetting station, a sorting station, a tube type identification station, and a sample quality determining station.

A method of recapping a sample container is presented. The method can be performed using a recapper described above. The method can comprises taking a foil out of a foil magazine. In one embodiment, the foil can be taken out by a vacuum device. The method can also comprise putting the foil in a foil transport element of a lever and rotating the lever such that the foil is positioned over the sample container, Referring initially to FIG. 1, FIG. 1 shows a recapper 100. The recapper 100 can comprise a lever arrangement 105 having, or comprising, a first lever 110 and a second lever 115. The first lever 110 and the second lever 115 can be arranged substantially horizontally and with an angle of about 180° between them.

The levers 110, 115 can abut each other just below a rotating device 140. The rotating device 140 can be adapted to rotate both levers 110, 115 substantially horizontally about a substantially vertical axis 142.

The rotating device 140 is shown as a vertical rod in FIG. 1 for the purpose of simplification. It can be understood that the rotating device 140 can typically be driven, for example, by an electric motor that is not shown in FIG. 1.

Below the lever arrangement 105, a sample container holder 120 can be arranged in which a sample container 125 can be held. The sample container 125 is shown exemplarily for a sample container on which a foil can be placed. The sample container 125 can partially be filled with a sample.

In the first lever 110, a first foil transport element 112 can be arranged. Similarly, a second foil transport element 117 can be arranged in the second lever 115. Both foil transport elements 112, 117 can similarly be embodied as through-holes with a respective step 113, 118 in the vertical middle of the respective lever 110, 115. This can allow a foil to be placed on the step 113, 118, while the foil can be loaded from above and can be unloaded from below the respective lever 110, 115. Exemplarily, a foil 127 in the second transport element 117 is shown.

Above the lever arrangement 105, a foil magazine 130 can be arranged. The foil magazine 130 can store a plurality of foils 135 that can be used for recapping sample containers. The foil magazine 130 can be replaced by a foil magazine handler 137 such that a new foil magazine can be installed in case the foil magazine 130 is empty. The foil magazine handler 137 is only shown schematically in FIG. 1.

Below the lever arrangement 105 and substantially vertically directly below the foil magazine 130, a vacuum device 150 can be arranged that can be placed on an elevator 155. The elevator 155 can allow the vacuum device 150 to be moved in the vertical direction just below the foil magazine 130.

Starting from the position shown in FIG. 1, the vacuum device 150 can be moved up until it abuts a foil 135 in the foil magazine 130. Then, a vacuum can be activated such that the foil 135 can be secured to the vacuum device 150. The vacuum device 150 can then move down until the foil 135 lies on the step 113 of the first foil transport element 112. Then, the vacuum can be deactivated and the vacuum device 150 can move further down below the lever arrangement 105. With such a process, a foil 135 can be taken out of the foil magazine 130 and can be placed into the foil transport element 112 for transporting the respective foil 135 to the sample container 125.

After having placed a foil into one of the foil transport elements 112, 117, the lever arrangement 105 can be rotated by about 180° using the rotating device 140. Then, this foil can be in a position as shown with the foil 127 in FIG. 1.

Above the lever arrangement 105 and vertically directly above the sample container holder 120, a heating device 160 can be arranged. The heating device 160 can be used in order to secure a foil on the sample container 125 by heat.

The rotation device 140 can be further adapted to move the lever arrangement 105 in the substantially vertical direction. Especially, starting from the state shown in FIG. 1, it can be possible to lower the lever arrangement 105 such that the foil 127 that is shown here in the second foil transport element 117 can abut the sample container 125 from above. Afterwards, the heating device 160 can heat up the foil 127 on the sample container 125 such that the foil 127 can be secured to the sample container 125 by heat.

After each such an operation of placing a foil 127 on a sample container 125, the lever arrangement 105 can be moved up again, a new foil 135 can be taken out of the foil magazine 130, can be brought to the sample container 125 and can be secured in the same way as just described. It can be noted that each of the foil transport elements 112, 117 can be loaded with a foil 127, 135 every time the respective foil transport element 112, 117 is moved from the foil magazine 130 to the sample container 125. This can allow for a very high throughput.

The recapper 100 can thus allow for a reliable and fast recapping of sample containers 125 with respective foils 127. Each recapping step can only take a very short amount of time. The sample container 125 can be exchanged by a sample container exchanger that is not shown in FIG. 1 such that an automatic operation in recapping of sample containers can be permitted.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A recapper for placing foils on laboratory sample containers, the recapper comprises:
   a foil magazine;
   a sample container holder horizontally distant from the foil magazine, the sample container holder adapted to hold a sample container;
   a lever arrangement comprising a plurality of levers, each lever comprising a foil transport element, wherein each foil transport element is a through-hole extending vertically through a corresponding lever with a landing for holding the foil inside the through-hole; and a rotating device, wherein each lever is attached to the rotating device such that with rotation of the rotating device, each lever rotates horizontally between a first orientation and a second orientation, wherein in the first orientation, the foil transport element of the lever is positioned at the foil magazine for collecting a foil from the foil magazine, and wherein in the second orientation, the foil transport element of each lever is positioned at the sample container holder to place the foil on the sample container.

2. The recapper according to claim 1, wherein the foil magazine is positioned above the lever arrangement.

3. The recapper according to claim 1, further comprising a vacuum device positioned below the lever arrangement for moving the foil from the foil magazine in a foil transport element.

4. The recapper according to claim 3, wherein the vacuum device is positioned directly below the foil magazine.

5. The recapper according to claim 3, wherein the vacuum device is adapted to move through the foil transport element to the foil magazine to abut the foil and to apply a vacuum to the foil for securing the foil to the vacuum device and the vacuum device is adapted to move down from the foil magazine in a position in which the foil is contained in the foil transport element and to release the foil by ceasing application of the vacuum.

6. The recapper according to claim 1, wherein the rotating device is adapted to vertically move the lever arrangement between an upper position and a lower position, wherein in the upper position, the lever arrangement can rotate freely, and wherein in the lower position, the foil contained in a foil transport element abuts a sample container.

7. The recapper according to claim 1, wherein the sample container holder is positioned below the lever arrangement such that the sample container held in the sample container holder is positioned below the lever arrangement.

8. The recapper according to claim 1, further comprising, a heating device positioned above the lever arrangement and operable to heat a foil after the foil has been brought into contact with a sample container by a lever.

9. The recapper according to claim 8, wherein the heating device is adapted to vertically move between an upper position and a lower position, wherein in the lower position, the heating device abuts a foil in contact with a sample container held in the sample container holder.

10. The recapper according to claim 1, wherein the levers of the lever arrangement are arranged with equal angle between each lever in a horizontal plane.

11. The recapper according to claim 1, wherein the lever arrangement comprises a first lever and a second lever and wherein the first lever and the second lever are arranged with an angle of 180° between the first level and the second lever in a horizontal plane.

12. The recapper according to claim 1, wherein the rotating device is solely adapted to rotate the lever arrangement by a specific angle in both rotating directions.

13. The recapper according to claim 12, wherein the specific angle is 180°.

14. A laboratory automation system, the laboratory automation system comprising:
a number of pre-analytical, analytical and/or post-analytical stations; and
a recapper according to claim 1, wherein the recapper is adapted to weld foils on sample containers containing samples that are to be processed, or have been processed, by one or more of the stations.

15. A method of recapping a sample container using a recapper according to claim 1, the method comprising:
taking a foil out of a foil magazine;
inserting the foil in a foil transport element of a lever;
rotating the lever such that the foil is positioned over the sample container;
lowering the lever such that the foil abuts the sample container; and
welding the foil on the sample container.

16. The method according to claim 15, wherein a vacuum device takes the foil out of the foil magazine.

17. The method according to claim 15, wherein a heating device welds the foil on the sample container.

* * * * *

UNITED STATES PATENT AND TRADEMARK OFFICE
CERTIFICATE OF CORRECTION

PATENT NO. : 10,435,187 B2  
APPLICATION NO. : 15/729066  
DATED : October 8, 2019  
INVENTOR(S) : Markus Hegel Page 1 of 1

It is certified that error appears in the above-identified patent and that said Letters Patent is hereby corrected as shown below:

On the Title Page

"Related U.S. Application Data" should read:  
(63) Continuation of application No. PCT/EP2016/059353, filed on Apr. 27, 2016

Signed and Sealed this  
Twenty-fifth Day of August, 2020

Andrei Iancu  
*Director of the United States Patent and Trademark Office*